US012648905B2

(12) United States Patent
Tir et al.

(10) Patent No.: US 12,648,905 B2
(45) Date of Patent: Jun. 9, 2026

(54) ORAL FILMS WITH FLAVOR ENTRAPMENT

(71) Applicant: INTELGENX CORP., St-Laurent (CA)

(72) Inventors: Billal Tir, Montréal (CA); Nadine Paiement, St-Laurent (CA)

( * ) Notice: Subject to any disclaimer, the term of this patent is extended or adjusted under 35 U.S.C. 154(b) by 0 days.

(21) Appl. No.: 18/098,683

(22) Filed: Jan. 18, 2023

(65) Prior Publication Data

US 2023/0225965 A1 Jul. 20, 2023

Related U.S. Application Data

(60) Provisional application No. 63/301,054, filed on Jan. 19, 2022.

(51) Int. Cl.
| | |
|---|---|
| *A61K 9/00* | (2006.01) |
| *A61K 31/05* | (2006.01) |
| *A61K 36/185* | (2006.01) |
| *A61K 47/10* | (2017.01) |
| *A61K 47/26* | (2006.01) |
| *A61K 47/46* | (2006.01) |

(52) U.S. Cl.
CPC .............. *A61K 9/006* (2013.01); *A61K 31/05* (2013.01); *A61K 36/3482* (2024.05); *A61K 47/10* (2013.01); *A61K 47/26* (2013.01); *A61K 47/46* (2013.01)

(58) Field of Classification Search
CPC ...................................................... A61K 9/006
See application file for complete search history.

(56) References Cited

U.S. PATENT DOCUMENTS

| | | | | |
|---|---|---|---|---|
| 4,695,463 | A | * | 9/1987 | Yang ........................ A23G 4/10 |
| | | | | 523/120 |
| 6,660,292 | B2 | | 12/2003 | Zerbe et al. |
| 7,132,113 | B2 | | 11/2006 | Zerbe et al. |
| 7,674,479 | B2 | | 3/2010 | Zerbe et al. |
| 8,575,194 | B1 | | 11/2013 | Schultz |
| 8,642,080 | B2 | | 2/2014 | Bender et al. |
| 8,691,272 | B2 | | 4/2014 | Zerbe et al. |
| 8,703,191 | B2 | | 4/2014 | Zerbe et al. |
| 8,735,374 | B2 | | 5/2014 | Zerbe et al. |
| 9,149,472 | B2 | | 10/2015 | Schultz |
| 9,301,948 | B2 | | 4/2016 | Zerbe et al. |
| 9,539,334 | B2 | | 1/2017 | Wood et al. |
| 9,668,970 | B2 | | 6/2017 | Obeid et al. |
| 9,717,682 | B2 | | 8/2017 | Zerbe et al. |
| 9,833,461 | B2 | | 12/2017 | Modi |
| 9,949,934 | B1 | | 4/2018 | Zerbe et al. |
| 10,272,038 | B2 | | 4/2019 | Obeid et al. |
| 10,406,186 | B2 | | 9/2019 | Finley et al. |
| 10,603,301 | B2 | | 3/2020 | Sinai et al. |
| 10,610,528 | B2 | | 4/2020 | Zerbe et al. |
| 10,722,476 | B2 | | 7/2020 | Zerbe et al. |
| 10,828,254 | B2 | | 11/2020 | Paiement et al. |
| 10,940,173 | B2 | | 3/2021 | Finley et al. |
| 11,033,493 | B2 | | 6/2021 | Obeid et al. |

| | | | | |
|---|---|---|---|---|
| 11,471,406 | B2 | | 10/2022 | Paiement et al. |
| 11,602,504 | B2 | | 3/2023 | Madwar et al. |
| 11,648,212 | B2 | | 5/2023 | Bilal et al. |
| 2001/0007680 | A1 | | 7/2001 | Kolter et al. |
| 2004/0131661 | A1 | | 7/2004 | Auffret |
| 2004/0156794 | A1 | | 8/2004 | Barkalow et al. |
| 2005/0107426 | A1 | | 5/2005 | Overeem et al. |
| 2006/0204559 | A1 | * | 9/2006 | Bess .................... A61K 47/585 |
| | | | | 424/443 |
| 2007/0053939 | A1 | | 3/2007 | Yokoyama |
| 2007/0190139 | A1 | | 8/2007 | Zerbe et al. |
| 2008/0057112 | A1 | | 3/2008 | Knoop et al. |
| 2009/0214640 | A1 | | 8/2009 | Szabo et al. |
| 2010/0297232 | A1 | | 11/2010 | Myers et al. |
| 2011/0136815 | A1 | | 6/2011 | Zerbe et al. |
| 2011/0142889 | A1 | | 6/2011 | Lee et al. |
| 2011/0263606 | A1 | | 10/2011 | Zerbe et al. |
| 2012/0141585 | A1 | | 6/2012 | Coulter |
| 2012/0156229 | A1 | | 6/2012 | Park et al. |
| 2013/0039932 | A1 | | 2/2013 | Park et al. |
| 2013/0177605 | A1 | | 7/2013 | Asari et al. |
| 2014/0065217 | A1 | | 3/2014 | Zerbe et al. |
| 2014/0155483 | A1 | * | 6/2014 | Li ........................... B29C 39/02 |
| | | | | 514/570 |
| 2015/0265720 | A1 | | 9/2015 | Levine et al. |
| 2016/0015683 | A1 | | 1/2016 | Mccarty |
| 2016/0022595 | A1 | | 1/2016 | Shikani et al. |
| 2016/0051510 | A1 | | 2/2016 | Allen et al. |
| 2016/0074396 | A1 | | 3/2016 | Jeon |
| 2016/0175245 | A1 | | 6/2016 | Brewer et al. |

(Continued)

FOREIGN PATENT DOCUMENTS

| | | |
|---|---|---|
| CA | 2489106 | 12/2003 |
| CA | 2535803 | 3/2005 |

(Continued)

OTHER PUBLICATIONS

Hughes, L. "Ion exchange resinates—the technology behind the mystery" 2005, Pharmaceutical Technology Europe, 17(4), 38-42 (Year: 2005).*

Vieira, E. et al., Evaluation of brewer's spent yeast to produce flavor enhancer nucleotides: influence of serial repitching, Aug. 20, 2013, Journal of Agricultural and Food Chemistry, vol. 61, 8724-8729 (Year: 2013).*

Sharma Vijay et al., Ion exchange resins and their applications, Journal of Drug Delivery and Therapeutics, 2014, vol. 4, 115-123 (Year: 2014).*

Bala et al., "Orally dissolving strips: A new approach to oral drug delivery system", Int. Journal Investig. Apr.-Jun. 2013;3(2): 67-76.

"Gum arabic", From Wikipedia, the free encyclopedia. [online] Retrieved from "http://en.wikipedia.org/w/index.php?title=Gum_arabic&oldid=767071650". Feb. 23, 2017.

Carrier oil and dosing, 2016 (Year: 2016). (The year of publication is sufficiently earlier than the effective U.S. filing date so that the particular month of publication is not an issue).

(Continued)

*Primary Examiner* — Bethany P Barham
*Assistant Examiner* — Paul Hoerner
(74) *Attorney, Agent, or Firm* — Anglehart et al.

(57) ABSTRACT

Pharmaceutical compositions employing flavor entrapment to mitigate the unpleasant taste of active agents are described.

17 Claims, No Drawings

(56) References Cited

U.S. PATENT DOCUMENTS

| | | | |
|---|---|---|---|
| 2016/0220480 A1 | 8/2016 | Bilal et al. | |
| 2016/0228385 A1 | 8/2016 | Sievers et al. | |
| 2016/0229845 A1 | 8/2016 | Cao et al. | |
| 2016/0243036 A1 | 8/2016 | Paiement et al. | |
| 2016/0324773 A1 | 11/2016 | Paiement et al. | |
| 2016/0346339 A1 | 12/2016 | Finley et al. | |
| 2017/0216220 A1 | 8/2017 | Bilal et al. | |
| 2017/0246120 A9 | 8/2017 | Stepovich | |
| 2017/0252300 A1 | 9/2017 | Modi | |
| 2017/0258710 A1 | 9/2017 | Conway et al. | |
| 2017/0290807 A1 | 10/2017 | Mundada | |
| 2017/0290870 A1* | 10/2017 | Schaneville | A61K 47/26 |
| 2017/0304319 A1 | 10/2017 | Westrin | |
| 2017/0333387 A1 | 11/2017 | Sarne | |
| 2018/0042890 A1 | 2/2018 | Sinai et al. | |
| 2018/0078549 A1 | 3/2018 | Zerbe et al. | |
| 2018/0110724 A1 | 4/2018 | Zerbe et al. | |
| 2018/0250240 A1 | 9/2018 | Paiement et al. | |
| 2018/0289665 A1 | 10/2018 | Turner et al. | |
| 2018/0303791 A1 | 10/2018 | Sinai et al. | |
| 2019/0060381 A1 | 2/2019 | Ballan et al. | |
| 2019/0133925 A1 | 5/2019 | Paiement et al. | |
| 2019/0209459 A1 | 7/2019 | Obeid et al. | |
| 2019/0231685 A1 | 8/2019 | Paiement et al. | |
| 2019/0247505 A1 | 8/2019 | Paiement et al. | |
| 2019/0290595 A1 | 9/2019 | Zerbe et al. | |
| 2019/0314293 A1 | 10/2019 | Bilal et al. | |
| 2019/0314326 A1 | 10/2019 | Garti et al. | |
| 2020/0054701 A1 | 2/2020 | Finley et al. | |
| 2020/0093786 A1 | 3/2020 | Sinai et al. | |
| 2020/0138730 A1 | 5/2020 | Madwar et al. | |
| 2020/0138885 A1 | 5/2020 | Paiement et al. | |
| 2020/0188348 A1 | 6/2020 | Sinai et al. | |
| 2020/0215063 A1 | 7/2020 | Zerbe et al. | |
| 2020/0268817 A1 | 8/2020 | Ballan et al. | |
| 2021/0015738 A1 | 1/2021 | Larosa et al. | |
| 2021/0036310 A1 | 2/2021 | Hou et al. | |
| 2021/0316347 A1 | 10/2021 | Klöckner | |
| 2021/0393611 A1 | 12/2021 | Madwar et al. | |
| 2022/0008381 A1 | 1/2022 | Garti et al. | |
| 2022/0031781 A1 | 2/2022 | Finley et al. | |
| 2022/0362164 A1 | 11/2022 | Paiement et al. | |
| 2022/0395452 A1 | 12/2022 | Paiement et al. | |
| 2022/0409584 A1 | 12/2022 | Bilal et al. | |
| 2023/0047314 A1 | 2/2023 | Paiement et al. | |
| 2023/0201130 A1 | 6/2023 | Madwar et al. | |
| 2023/0248660 A1 | 8/2023 | Bilal et al. | |

FOREIGN PATENT DOCUMENTS

| | | |
|---|---|---|
| CA | 2910206 | 12/2015 |
| CA | 2922959 | 6/2016 |
| CA | 3017264 | 9/2017 |
| CA | 3020798 | 10/2017 |
| CA | 2998218 | 4/2018 |
| CA | 3044248 | 5/2018 |
| CA | 3056944 | 10/2018 |
| CA | 3067822 | 12/2018 |
| CA | 3017526 A1 | 3/2020 |
| CN | 106176685 A | 12/2016 |
| EP | 0743064 A1 | 11/1996 |
| WO | 9940898 | 8/1999 |
| WO | 2005120256 | 12/2005 |
| WO | 2007052121 | 5/2007 |
| WO | 2008038155 A2 | 4/2008 |
| WO | 2012121461 A1 | 9/2012 |
| WO | 2013107810 A1 | 7/2013 |
| WO | 2016123475 | 8/2016 |
| WO | 2016134454 A1 | 9/2016 |
| WO | 2018061007 | 4/2018 |
| WO | 2018176149 A1 | 10/2018 |
| WO | 2018205017 A1 | 11/2018 |
| WO | 2020051709 A1 | 3/2020 |
| WO | 2022165607 A1 | 8/2022 |
| WO | 2022170442 A1 | 8/2022 |

OTHER PUBLICATIONS

Morepen, The Joy of Growing Together, [online] Retrieved from "http://www.morepen.com/api-product-information.htm". (2010). (The year of publication is sufficiently earlier than the effective U.S. filing date so that the particular month of publication is not an issue).

Okumu et al., "Dynamic Dissolution Testing to Establish In Vitro/In Vivo Correlations for Montelukast Sodium, a Poorly Soluble Drug", Pharmaceutical Reasearch, vol. 25, No. 12, Dec. 2008.

Raghavendra Rao N. G et al., "Development of Mucoadhesive Films for Buccal Administration of Montelukast", IJPT, Mar. 2010, vol. 2, Issue No. 1, 1-15.

Venkateswarlu et al., "Preparation and Evaluation of Fast Dissolving Buccal Thin Films of Bufotenin", iMedPub Journals (Dec. 5, 2016), vol. 2, No. 4:12.

Balakrishnan, P., et al. Enhanced oral bioavailability of Coenzyme Q10 by self-emulsifying drug delivery systems. International Journal of Pharmaceutics, (2009), 374(1-2), 66-72.

Hallucinogens: LSD, Peyote, Psilocybin, and PCP. National Institute on Drug Abuse (2008).

Baliga, S. et al. "Salivary pH: A diagnostic biomarker". J Indian Soc Periodontol, 17(4) :461-465 (Jul.-Aug. 2013).

Khatoon, N. et al. "Formulation and evaluation of oral fast dissolving films of montelukast sodium". International Journal of Pharmaceutical Sciences and Research, 5: 1780-1787 (May 2014).

The Dow Chemical Company, "Hydroxyethyl Cellulose" (Mar. 2002).

López-Olaondo et al. "Combination of ondansetron and dexamethasone in the prophylaxis of postoperative nausea and vomiting". British Journal of Anesthesia (1996), 76, 835-840.

Eleftheriadis, Georgios K. et al. Unidirectional drug release from 3D printed mucoadhesive buccal films using FDM technology: In vitro and ex vivo evaluation. European Journal of Pharmaceutics and Biopharmaceutics 144 (2019) 180-192.

English Translation of WO2012121461A1, published Sep. 13, 2012. Machine Translation.

Vishvakarma, "Design and development of montelukast sodium fast dissolving films for better therapeutic efficacy", Journal of the Chilean Chemical Society, 63(2), pp. 3988-3993, Jun. 1, 2018 (Jan. 6, 2018).

* cited by examiner

ORAL FILMS WITH FLAVOR ENTRAPMENT

CROSS REFERENCE TO RELATED APPLICATIONS

This present application claims priority to U.S. Provisional Patent Application No. 63/301,054, which was filed on Jan. 19, 2022, and is hereby incorporated by reference in its entirety.

FIELD OF THE DISCLOSURE

This disclosure relates to oral dosage forms for administration of an active agent, and more particularly to films containing an active agent or excipient having an undesired taste. This disclosure also relates to methods of making oral film-type dosage forms that employ a resin that entraps a flavoring agent to mitigate the unpleasant taste of an active.

BACKGROUND OF THE DISCLOSURE

Film-type oral dosage forms are often preferred by subjects that have difficulty swallowing tablets or capsules. Such drug delivery options can allow the medication to bypass the first pass metabolism thereby making the medication more bioavailable. As the strip dissolves, the drug can enter the blood stream enterically, buccally or sublingually. Film-type dosage forms are designed for oral administration, with the user placing the strip on or under the tongue (sublingual) or along the inside of the cheek (buccal). Oral films eliminate some common problems associated with drug administration such as the fear of choking and the need for water intake. Oral films also offer significant benefits to those subjects wanting to administer the medication in a discreet, inconspicuous, unnoticeable and/or private manner, especially while in the company of others. Such oral films are also particularly useful for geriatric, pediatric and veterinary subjects.

It is important, however, that the film dissolve or disintegrate rapidly without leaving a gritty residue or undesired taste. Thus, developing an oral film-type dosage form that can achieve instant wettability and rapid disintegration, while exhibiting good mouthfeel is desirable. Oral film ("OF") dosage forms as opposed to other dosage forms such as tablets, injectables and transdermal patches have the inconvenience of making the active agents' taste readily exposed to the subject's taste receptor, thus promoting the tasting of actives by the subject. This taste has the potential to decrease the repeated use of the oral film dosage form by certain subjects. There is thus a need for an OF capable of effectively mitigating the undesirable taste arising from the naked active in the subject's mouth. This disclosure relates to disintegrating films for oral administration of an active agent, and more particularly to films of this type that exhibit instant wettability.

Encapsulation or coating of the active in tablets, pills or capsules tends to prevent or minimize direct contact of the active with the subject's taste bud receptors, but this encapsulation or coating will be lost when the said solid dosage forms are scored or crushed and imbedded in foods for populations with difficulty swallowing. In addition, since many children and elderly cannot or will not swallow solid dosage forms such as tablets, pills or capsules, the oral film dosage is the preferred alternative to administer oral dosage forms in pediatric and elderly populations, and it is an alternative that does not affect active ingredient protection if the film is cut to lower size. Applicability exists as well in the veterinary field, particularly in dogs, which have a sensitivity to taste that is 400 times greater than that of humans.

An oral film dosage having a bad aftertaste increases the odds of rejection by the patient and hampers patient compliance with prescribed treatments. Whether or not the active's or excipient's bad aftertaste remains in the patient's mouth for a prolonged period of time, the compliance and the efficacy of the treatment are typically compromised by any perceived undesired taste. Drug side effects like nausea and vomiting may also be induced by a patient's exposure to a bad aftertaste.

In oral film technologies, attempts have been made to find optimal solutions to mask, cover or otherwise eliminate unpleasant tasting active ingredients. Developing an oral film without masking the aftertaste may employ alternative processes such as micro-encapsulation of the active to diminish the interaction between the active and the taste buds, as in WO2007052121A2. Micro-encapsulation of the active has several limitations for an OF such as delay of drug release in oral mucosa, which in turn may delay the time needed to reach the maximum concentration of the active in the blood for efficacy. This is particularly important in instances where the active must be absorbed buccally in part or in its entirety to avoid the first hepatic pass.

Another potential limitation of micro-encapsulation is the increase of solids and corresponding increase in film size that affects the feasibility of the film dosage form. In this case, there is risk of premature release of the active in the oral cavity due to encapsulation wall imperfection or deficiencies during the blending process. The result being that a part of the active is exposed in the finished product. It is difficult to incorporate an encapsulated active in an OF formula without exposure to the liquid mass of the blend.

A mitigating approach is to sprinkle the encapsulated active onto the coated wet film before drying, or to spray liquid containing the encapsulated active onto the coated dry film, but such techniques will not produce distribution uniformity of the active in the finished product, which may increase drug variability during manufacturing. Another mitigating approach is to use smooth mixing of the encapsulated active with wet film blend usually having solvent non dissolving the encapsulated active, and use continuous recirculation mode from up to down and when the blend becomes homogeneous, to coat the obtained mixture. However, such an approach may require lower viscosity for the blend mixture to ensure quick homogeneity, then to increase the viscosity by varying the pH or adding a thickening agent, or to use polymers with shear thickening properties to prevent sedimentation and ensure uniformity of distribution of the active ingredient. Even in this case, the encapsulation might have a high risk of becoming defective because of the mixing and transfer.

Another alternative is to prepare a multilayer oral film where a mix of encapsulated active and blend made of at least one film forming polymer and preferable non dissolving solvent for the encapsulated active are mixed together to form the active layer then coated on dry film layer called a support. Once the bilayer film is dried, optionally a third film layer called a cover is laminated with the previous layer to cover the active layer, or a film blend is coated on top of the active layer of the previous film bilayer. With this approach, the active ingredient will get double protection to prevent exposure of bad taste. But this technique is not suitable for immediate release drug delivery or for buccal absorption, besides that it is particularly time consuming, and may not be economical. A further disadvantage is the increased ratio of solids that increase the film size and additionally present high risk of damaging the shell of the encapsulated active. Therefore, the resultant films will have poor uniformity of content.

Active agent aftertaste mitigation is challenging when formulating oral film dosage forms, particularly since the unpleasant taste is perceived by the subject as soon as the active agent enters in contact with the taste buds. Other known techniques used to cover the perceived unpleasant taste of active agents include the addition of flavoring agents or compounds, taste maskers, cooling agents, local anesthesia agents, sweeteners and flavor enhancers. Flavor enhancers have a limited ability to control the flavor profile and often fail to mitigate the perceived unpleasant aftertaste. It is difficult to alleviate lasting undesired taste since sweeteners, flavoring agents and taste maskers are released in the buccal environment while the oral film matrix dissolves or disintegrates, meaning they may act on different receptors to mitigate the undesired bad taste signal or compete with the active for the same binding taste receptors. In addition, the cooling agents and/or local anesthesia agents will act on the entire buccal cavity, which will result in an oral film not adequate for pediatric use.

In a multilayer orals film ("MOF"), at least one layer is designed to control flavoring agent release to cover the perceived unpleasant aftertaste of the active. However, this approach makes MOF residence time longer and gives rise to another issue, bad mouthfeel. This approach with MOF are not feasible for OF designed for buccal absorption since the active layer will be not in direct contact with the mucosa. Quick disintegrating MOFs cannot readily be designed with this approach, since the additional layer defeats the purpose of having a film that readily dissolves or disintegrates.

Another issue that arises when attempting to cover an active's unpleasant aftertaste using known techniques lies in the ability of the active's unpleasant taste or aftertaste to saturate the taste bud receptors. In this case, the film residues in the mouth carrying the active in the buccal environment may have a delayed effect on the taste bud receptors.

Flavor micro-encapsulation, which provides flavoring agents entrapped inside a carrier to control flavoring agent release and make the flavoring agent available at a desired site and time and at a specific rate, is useful to mask the undesired taste during the entire residence time of the OF in the buccal environment. The release of the flavoring agent from the microcapsule is controlled by at least one of the following mechanisms: diffusion of flavoring agent through the capsule carrier wall, degradation, swelling or melting of the capsule carrier wall. Since film manufacturing technology involves a shearing process, the manufacturing of OFs will typically compromise the wall of the encapsulated flavoring agent and affect the release of the flavoring agent from the OF in the buccal environment. In this way, adding protection with a carrier wall to the flavoring agent will delay or prevent flavoring agent release.

In addition to the abovementioned issues, high active loading oral dosage forms having an undesired or unpleasant taste present an even more significant challenge in OF formulation. Prior publications have described strategies to reduce the contact time between actives and the taste buds, and/or to add flavoring agents, masking agents, cooling agents and/or local anesthesia agents that attempt to cover the bad aftertaste.

In US2008057112 A1, it is disclosed to add at least one vitamin, mineral and flavoring agent sufficient to mask the bad taste. In WO05120256 A2, it is disclosed to add a pureed natural extract from a fruit or vegetable to the film formulation. In US2012156229 A1, it is disclosed to add a stevioside-based sweetener to the film formulation to mask the taste of a given active. In this prior art, there is only one stage of flavoring agent release which will not mitigate the aftertaste that typically occurs and last after the active ingredient of bad taste has been released from the dosage form.

Other proposed solutions to cover a high concentration of an unpleasant tasting compound include i) coating the active by encapsulation to delay drug release in the mouth as for example in US2001007680 A1. This solution is limited in OFs by the amount of solids that can be incorporated in an OF by their nature and it is not a suitable solution if a quick onset of action is required; and ii) the complexation of the active with cyclodextrins, as the coating encapsulation of the active is again limited by the solid content in the OF. In this method, use of flavoring agent(s) and or bitter masks competes for the taste buds as the active's receptors, and are released before the active in the buccal environment. This method coats the active together with the flavoring agent and/or bitter mask and introduces the active at a lower solubility state as suspended or uses pH effects to neutralize active charges (in the case of an ionizable active) to avoid its interaction with taste buds.

Even with the combination of aforementioned strategies, the high concentration of unpleasant active still risks reaching the taste buds and causing an unpleasant aftertaste. Therefore, there is a useful reason for adapting the release of the flavoring agent during and after the residence time of the active in the buccal environment.

SUMMARY OF THE DISCLOSURE

According to some aspects of the disclosure, it is disclosed oral film formulations designed for entrapping flavoring agents in oral films and methods for making oral film dosage forms with entrapped flavoring agents therein.

According to some aspects of the disclosure, the oral film formulations have an effective amount of at least one free flavoring agent, one resin entrapped flavoring agent and a bad taste or unpleasant-tasting active ingredient or excipient in an oral film dosage form.

According to some aspects of the disclosure, the flavoring agent used in the flavor entrapped OFs are dry flavoring agents, liquid flavoring agents or a combination of both dry and liquid flavoring agents.

According to some aspects of the disclosure, the oral film formulations cover or at least partially mitigate the perceived aftertaste of an active agent while providing delayed flavoring agent release, thus mitigating the perceived undesired aftertaste of an active that typically occurs after the taste stimulus (i.e., the unpleasant tasting active or excipient) has been removed from the oral cavity.

According to some aspects of the disclosure, it is disclosed a method for optimizing flavors by mitigating flavoring agent evaporation during oral film manufacturing. Flavor optimization according to this disclosure is achieved by entrapping flavoring agents using resins to mitigate flavor evaporation or loss of flavors during manufacturing of oral film dosage, mainly during blending, coating, drying and packaging, more particularly during the drying phase of the process while providing the desired flavor in a reproducible fashion.

The entrapment of the flavoring agents inside resin pores makes flavoring agents available in a more concentrated form once the subject takes the film. Increasing the concentration of the available flavoring agent(s) is desired to make a potent impact on taste buds receptors.

According to further aspects of the disclosure, it is disclosed an oral film formulation designed to deliver the flavoring agent to mitigate the perceived taste of a component of the oral film formulation.

According to aspects of the disclosure, it is disclosed an oral film formulation designed to deliver the flavoring agent to maintain the flavor intensity profile over time to mitigate the perceived taste of a component present in the oral film formulation.

According to aspects of the disclosure, it is disclosed an oral film formulation designed to entrap flavoring agents via the integration of resins to cover the aftertaste, and in some instances to provide extended flavor release, thus mitigating the undesired flavor perceived when consuming an OF wherein one of its components exhibits an unpleasant taste.

Preferably, the oral film formulation comprises flavoring agents in an amount sufficient to mitigate the taste of the active, where the active has an unpleasant taste or an aftertaste.

Also disclosed are particular embodiments in which a desirable flavor profile is enhanced by the addition of flavor enhancers with or without yeast derivatives.

Also disclosed are particular embodiments in which undesirable tastes are mitigated by the addition of taste maskers with or without sweetener(s).

In general, a pharmaceutical composition can be dispensed from a device. The device can dispense a pharmaceutical composition in a predetermined dose as a film.

According to another aspect of the present disclosure there is provided an oral dosage form and a method of preparation thereof, comprising at least one of the following: resin entrapping a flavoring agent, a free flavoring agent and one active. The active may or may not be entrapped with the flavoring agent.

Another aspect of the disclosure also provides for a method that includes administering the oral dosage form described herein to a patient in need thereof. The administration is carried out, in an amount and for a period, effective to treat the patient's condition or symptom. The patient may be a human or an animal.

Another aspect of the disclosure provides for a dissolvable and/or disintegrable film that possesses one or more advantages. The one or more advantages can be attributed, at least in part, to a mitigation of bad tastes in the administration of at least one active.

These and other features, advantages and objects of the various embodiments will be better understood with reference to the following specification and claims.

DETAILED DESCRIPTION OF THE DISCLOSURE

The present disclosure contemplates a rapidly dissolving oral film that will adhere to the oral cavity, releasing one or more active agents that has the potential to cause an unpleasant initial taste, aftertaste and/or bad mouthfeel. Such unpleasant taste is mitigated by using a resin-entrapped flavoring agent and at least one free flavoring agent. Optionally, the formulation may contain a combination of certain plasticizers or surfactants, colorants, sweetening agents, flavoring agents, flavor enhancers, or other excipients commonly used to modify the taste of formulations intended for application to the oral cavity.

Film systems embody a field of technology that has major advantages in areas of administering various actives to an individual in need thereof. The present disclosure relates to oral films and methods for forming film products that include at least one active. Specifically, the disclosure provides for an oral film and a method of forming an oral film that minimizes or eliminates the unpleasant taste associated with a given active or excipient, ensuring patient compliance.

The terms "oral dissolving film," "oral dissolvable film", "oral disintegrating film", OSF, "oral soluble film", "ODF", "oral chewable film", "OCF", "oral thin film", "OTF," "oral wafer", "oral drug strip" or "oral strip" refer to a product used to administer a predetermined amount of active ingredient(s) via oral administration such as oral transmucosal absorption, sublingual delivery or buccal delivery and will be referred to throughout as oral film(s), denoted "OF".

The term "film" refers to a type of dosage form that is distinctly different from pills, tablets, caplets, and capsules, and in which the dosage form is a thin strip of material. It will be understood that the term "film" includes delivery systems of various thickness, including films, film strips, discs, sheets, stamp, and the like, in any shape. Such films are typically rapidly disintegrating or rapidly dissolving, but can also exhibit longer disintegration times when required. The films are generally sufficiently flexible to allow bending or even folding without breaking. For example, the films typically have length and width dimensions on the order of 5 to 35 mm, although larger or smaller dimensions are possible and may be desirable in particular circumstances, and a thickness on the order of 5 to 300 μm, although larger or smaller thicknesses are possible and may be desirable in certain circumstances.

Any number of active agents or active pharmaceutical ingredients may be included in the films discussed herein. The term "active(s)" or "active agent(s)" refers mainly to active pharmaceutical ingredients (APIs), but may also refer generally to any agent(s) that chemically interacts with the subject to which it is administered to cause a biological change, such as, but not limited to, eliminating symptoms of disease or regulating biological functions. The term "pharmaceutical ingredient or API" and variations thereof generally refers to any agent that is being administered orally to a subject and includes pharmaceutical active agents, nutraceutical active agents, and breath freshening agents. Examples of pharmaceutical active agents include ACE-inhibitors, antianginal drugs, anti-arrhythmics, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, tadalafil, and vardenafil, fertility agents, gastrointestinal agents, homeopathic remedies, hormones, hypercalcemia and hypocalcaemia management agents, immunomodulators, immunosuppressives, anti-migraine preparations such as rizatriptan, eletriptan and zolmitriptan, motion sickness treatments, muscle relaxants, obesity management agents, osteoporosis preparations, oxytocics, parasympatholytics, parasympathomimetics, prostaglandins, psychotherapeutic agents, respiratory agents, sedatives such as lorazepam or diazepam, smoking cessation aids such as bromocryptine or nicotine, sympatholytics, tremor preparations, urinary tract agents, vasodilators, laxatives, antacids, anti-pyretics, appetite suppressants, expectorants, anti-anxiety agents such as alprazolam, anti-ulcer agents, anti-inflammatory substances, coronary dilators, cerebral dilators, peripheral vasodilators, psycho-tropics, stimulants, anti-hypertensive drugs, vaso-constrictors, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, cannabinoid, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof. Examples of nutraceutical active agents include various dietary supplements, vitamins, minerals, herbs and nutrients.

The term "cannabinoid" represents a group of C21 terpenophenolic compounds found uniquely in cannabis plants. Cannabinoids include the psychoactive compounds Δ9-tetrahydrocannabinol (THC), Δ8-THC, cannabinol (CBN), 11-hydroxy A9-THC, anandamide, and the non-psychoactive compounds cannabidiol (CBD), cannabichromene, and (–) Δ8-THC-11-oic acid. The term cannabinoid is used herein to refer to a cannabinoid that is either synthetic or extracted from the plant. It is also used to refer to a single cannabinoid or mixture of cannabinoids. The term "cannabis" is used to refer to plants of the genus *Cannabis*, including *Cannabis sativa* and *Cannabis indica*.

The term "instantly wettable" and variations thereof generally refers to the ability of the film dosage form to rapidly imbibe moisture upon oral administration to a subject and immediately soften, whereby the subject is prevented from experiencing a prolonged adverse feeling in the mouth, and with respect to certain aspects of the disclosure refers to embodiments in which moisture (i.e., water) applied to a surface of the film penetrates the thickness of the film (e.g., typically about 5 μm to 200 μm) within 5, 10, 15 or 20 seconds.

The term "mucoadhesive" and variations thereof generally refers to film matrix or pharmaceutical dosage form interacting by means of adhesion with the mucus that covers epithelia.

The term "rapidly disintegrating" and variations thereof generally refers to the ability of the film dosage forms to break up into submicron particles or completely dissolve within an acceptable period of time (e.g., within 60 seconds, within 45 seconds, within 30 seconds, within 20 seconds, or within 15 seconds of being administered, i.e., placed in the oral cavity of a subject).

The terms "blend" or "blending media" and variations thereof generally refers to the combination of the OF formulation with the presence of at least one solvent.

The term "loading media" and variations thereof generally refers to the liquid phase where occurs the reaction of complexation (loading) of the guest (e.g., "resin") with the ligand (e.g., flavoring agent, drug substance) to form the "resinate" (resin complex).

The term "resin" and variations thereof generally refers to any of a class of solid or semisolid organic products of natural or synthetic origin with no definite melting point, generally of high molecular weight; most resins are polymers. Examples of resin include but are not limited to ε-poly-L-lysine beads, cholestyramine, polyox, methacrylic resins like Eudragit®, Colestipol and others or mixtures thereof.

The term "ion exchange resin" and variations thereof generally refers to a solid resin material containing a network of ions that are exchangeable with other ions with a like charge that are present in a solution in which the resin is insoluble. Resins are insoluble polymers that contain acidic or basic functional groups and have the ability to exchange counter-ions within aqueous solutions surrounding them. Based on the nature of the exchangeable ion of the resin as a cation or anion, it is classified as cationic or anionic exchange resins, respectively. The efficacy of ion exchange resins mainly depends upon their physical properties such as degree of cross-linking, porosity, acid base strength, stability, purity and particle size. Examples of ion exchange resins include but are not limited to Amberlite IRP69, Duolite AP143, Amberlite IRP88, Amberlite IRP64, and others or mixtures thereof. There are different categories of ion exchange resins: Strong acid cation exchange resins, which are used to remove positively charged ions such as calcium, magnesium, and iron from water; Weak acid cation exchange resins, which are used to remove positively charged ions such as hydrogen and ammonium from water; strong base anion exchange resins, which are used to remove negatively charged ions such as chloride, sulfate, and nitrate from water; Weak base anion exchange resins, which are used to remove negatively charged ions such as carbonate, hydroxide, and bicarbonate from water; Chelating resins, which are used to remove metal ions from solutions; and Mixed-bed resins, which are a combination of cation and anion exchange resins used to purify water to a high degree.

The term "aftertaste" and variations thereof generally refers to the taste that is perceived following the intake of an OF, after the initial taste. Aftertaste is understood as the lasting taste that remains once the film has been entirely dissolved and/or disintegrated and none of the film remains in the subject's or consumer's buccal cavity.

The term "taste masker" and variations thereof generally refers to an ingredient capable of covering or at least making more acceptable an unpleasant odor or taste in a food or pharmaceuticals. Of the many tastes that must be masked in pharmaceuticals, bitterness is most often encountered; to mask it completely is challenging. Examples of bitter maskers include but are not limited to licorice, coffee, chocolate, mint, grapefruit, cherry, peach, raspberry, orange, lemon, lime, advantame and others or mixtures thereof.

Syrups of cinnamon, orange, citric acid, cherry, cocoa, wild cherry, raspberry, or glycyrrhiza elixir, raspberry and other fruit syrups can be used to effectively mask salty and bitter tastes in a number of drug products. Metallic tastes in oral liquid products (e.g., iron) are usually masked by extracts of guarana, a tropical fruit, but can be masked by other extracts and agents The term "flavor" and variations thereof generally refers to the entire range of sensations evoked by a substance in the mouth when we eat a food or drink a beverage. Flavor encompasses a substance's taste, smell, and any physical feeling we perceive in our mouths, such as "heat" (for example, cinnamon) or "cold" (for example, spearmint).

The term "flavoring agents" and variations thereof generally refers to concentrated preparations, with or without flavor adjuncts required in their manufacture, used to impart flavor, with the exception of salt, sweet, or acid tastes. Flavoring agents may be classified as natural, artificial, or natural and artificial (N&A) by combining the all-natural and synthetic flavors or other forms known in the art.

Flavoring agents are categorized by their physical classification as solid flavoring agents and liquid flavoring agents, with or without encapsulation to preserve the heat sensitive or volatile flavoring agents during drying process.

The term "natural flavors" and variations thereof generally refers to flavoring agents that come from natural sources such as a spices, fruits, or vegetables. They can also come from herbs, barks, roots, or similar plant materials. Natural flavors also come from meat, seafood, poultry, eggs, and dairy products. Flavors are only used to add taste to foods; they are not nutritional in their definition.

The term "artificial flavors" and variations thereof generally refers to flavoring agents that do not meet the definition of natural flavor. The chemical compositions of natural and artificial flavorings do not usually differ considerably; it is the source that differs. Active ingredients in natural flavors used to impart flavor are often identified and reconstructed synthetically with reasonable accuracy.

The term "natural & artificial (N&A) flavors" and variations thereof generally refers to natural flavors combined with synthetic ingredients to enhance flavor balance and fullness. These flavors are generally classified according to type and taste sensation.

The term "WONF (With Other Natural Flavors) flavors" and variations thereof generally refers to blends of juices or juice concentrates where at least 50% of the flavor is derived from the named fruit and not more than 50% from other natural flavors. In practice, this can describe the addition of juices to those indicated as the characterizing flavor.

The term "liquid flavor" and variations thereof generally refers to a flavor in liquid phase with or without liquid carrier. The texture is generally dependent on the solvent within which they are prepared. Liquid flavors are available both as oily (e.g., essential oils) or non-oily liquids. Examples of liquid flavor include but are not limited to essential oils, fluid extracts, tinctures, and distillates or other forms known in the art. The term "liquid" and variations thereof generally refers to viscous liquids, slurries, foams, pastes, gels and the like.

The term "distillates" and variations thereof generally refers to a clear, flavorful liquid produced from fruits, herbs, roots, etc., by heating and condensing vapor. A distilled concentration of raw material yields essential oils, which separate from the aqueous phase in the receiver when the distillate condenses.

The term "essential oils" and variations thereof generally refers to a volatile substance obtained from plant materials by distillation. After condensation of the vapor phase, the oil separates from the aqueous phase and is removed. Essential oils are used to create flavors. Characteristic aromas of the plant material are generally complex mixtures of organic chemicals and are insoluble. Example of essential oils include but are not limited to thymol, eugenol, eucalyptus, tea tree oil, oil of wintergreen, oil of pepper mint, oil of spearmint, clove bud oil, menthol, anethole, methyl salicylate, cassia, sage, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and others or mixtures thereof.

The term "extract" and variations thereof generally refers to a solution composed specifically of compounds that create flavors obtained by passing alcohol, or an alcohol-water mixture, through a substance. Extracts found on the grocer's shelf, such as orange, almond, lemon, etc. are essential oils dissolved in an alcohol-water mixture. The flavor extract may include fruit extracts, botanical extracts, spice extracts, and mixtures thereof. Exemplary fruit extracts include citrus extracts (e.g., extracts of orange, mandarin orange, tangerine, tangelo, pomelo, lemon, lime, and grapefruit, among others), berry extracts (e.g., extracts of blackberry, blueberry, boysenberry, cranberry, raspberry, and strawberry, among others), and extracts of apple, grape, cherry, pineapple, plum, prune, fig, pineapple, peach, banana, pear, guava, apricot, coconut, olive, kiwi, quince, passion fruit, pomegranate, persimmon, mango, rhubarb, papaya, lychee, currant, and date, or mixtures thereof. Exemplary botanical extracts include extracts of kola nut, tea, coffee, cocoa, hazelnut, almond, or mixtures thereof and others. Exemplary spice extracts include extracts of cassia, clove, cinnamon, pepper, ginger, vanilla, cardamom, coriander, root beer, sassafras, ginseng, and others or mixtures thereof.

The term "tinctures or tinctura" and variations thereof generally refers to an alcoholic extract of a botanical material without further processing. Tinctures are obtained by maceration or percolation of specific herbs and spices in alcohol in which the aroma is preserved. The tinctures may include orange peel, lemon peel, wild cherry, aloe, ambergris, ambrette seed, blackberry, cacao, cinnamon, cloves, cumin, ginger, mandarin, origanum, paprika, peppermint, and others or mixtures thereof.

Cooling agents in oral film pharmaceuticals are substances that provide a cooling sensation in the mouth when the film is applied. Some examples include menthol and eucalyptus oil.

The term "aroma" and variations thereof generally refers to the odor or fragrance of a flavor. Aroma (or smell or odor) is the sensation perceived when volatile compounds are sniffed through the nose. An aroma chemical may include any chemical designated by the Flavor and Extract Manufacturers' Association (FEMA) to be Generally Recognized As Safe (GRAS). A chemical designated as GRAS by FEMA has been tested using certain standards and deemed safe for use by humans. Exemplary GRAS aroma chemicals include acetic aldehyde, acetic acid, Isoamyl acetate, 3-methylbutanol, isoamyl butyrate, isoamyl hexanoate, isoamyl isovalerate, benzaldehyde, benzoic acid, benzyl acetate, benzyl alcohol, benzyl cinnamate, butyl acetate, isobutyl acetate, butanol, isobutanol, butyl butyrate, isobutyl butyrate, butyl isobutyrate, butyl hexanoate, isobutyl propionate, butyraldehyde, isobutyraldehyde, butyric acid, isobutyric acid, cinnamaldehyde, cinnamic acid, 2,3-butanedione, ethyl acetate, ethyl acetoacetate, ethyl benzoylacetate, ethyl butyrate, ethyl isobutyrate, ethyl cinnamate, ethyl heptanoate, ethyl hexanoate, ethyl lactate, ethyl 2-methylbutyrate, ethyl propionate, ethyl pyruvate, ethyl valerate, ethyl isovalerate, 2-heptanone, hexanal, hexanoic acid, hexanol, raspberry ketone, $\alpha$-ionone, $\beta$-ionone, lactic acid, 2-methylbutyraldehyde, isovaleraldehyde, 2-methylbutyric acid, methyl cinnamate, methyl 2-methylbutyrate, methyl propionate, propionaldehyde, propanoic acid, propanol, pyruvic acid, valeric acid, isovaleric acid, vanillin, 4-methyl-5-hydroxyethyl thiazole, acetone, heptanoic acid, 2-methylbutyl 2-methylbutyrate, 2-isopropyl-5-methyl-2-hexenal, ethyl 3-hydroxybutyrate, 2-methylbutyl isovalerate, isoamyl isobutyrate, tiglic acid, D-2-methylbutyl acetate, L-2-methylbutanol, methanol, cyclopentadecanone, acetic anhydride, and other compounds. GRAS aroma chemicals may be extracted from natural sources or produced synthetically.

The term "solid flavor" and variations thereof generally refers to flavor in solid phase or flavor formula in solid carrier. Several principle techniques have been proposed for the preparation of solid flavoring materials. Solid flavors include but are not limited to crystalline flavor, microencapsulated flavor and powder flavor that are spray-dried, freeze-dried flavor powder, dried extract flavor, plated flavor, and mixtures thereof. Exemplary solid flavors include crystalline vanillin, freeze-dried cinnamon powders, and dried lemon fluid extract, and others or mixtures thereof.

The term "flavor enhancer" and variations thereof generally refers to compounds that particularly enhance certain tastes or reduce undesirable flavors without having an especially strong taste of their own. They harmonize taste components and make food/drug preparations more palatable. Examples include but are not limited to maltol, ethyl maltol and monosodium glutamate, glutamic acid, glutamates, purine-5-ribonucleotides, inosine, guanosine, adenosine 5_-monophosphates, sugars, sweetener, carboxylic acids (e.g., citric, malic, and tartaric), common salt (NaCl), amino acids, some amino acid derivatives (e.g., monosodium glutamate-MSG), and spices (e.g., peppers) are most often employed, yeast, yeast extract, dried yeast and others or mixtures thereof.

The term "non-water-soluble flavoring agent" and variations thereof generally refers to practically insoluble, or insoluble flavoring agents that will not substantially dissolve in water even after mixing at given concentration, temperature, and pressure. Insolubility in water may be judged visually by the lack of the compound disappearance and forming one phase in a test-tube of water at a given content, temperature, and pressure. Examples of non water-soluble flavoring agents include but are not limited to eucalyptol, eugenyl acetate, farnesene, farnesol, d-fenchone, 2-benzofuran carboxaldehyde, benihinal, geranyl valerate, rosin, lemongrass oil, limonene, tributin, resins of oleoresin ginger, and others or mixtures thereof.

The term "suspended flavor" and variations thereof generally refers to dispersions of an insoluble solid flavor composition or flavoring agent in a liquid phase to make a suspension. For a successful suspension, insolubility of the flavor composition or flavoring agent is required. Examples of water suspended flavor include but are not limited to acetanisole, 2-decylfuran, dehydrodivanillin, eugenyl benzoate, benzofuran-2-carboxaldehyde, and others or mixtures thereof.

The term "ionizable flavoring agent" and variations thereof generally refers to the tendency of a flavouring molecule to be ionized (becomes an ion) by losing or gaining electrons in solution where the molecule acquires a net charge and becomes an ion. Changing the pH of the solution may be the simplest and most effective means of increasing the solubility. Examples of ionizable flavoring agents include but are not limited to amyl benzoate, isoamyl butyrate, isoamyl cinnamate, guaiacyl phenylacetate, vanillin, and others or mixtures thereof.

The term "sweetener" and variations thereof generally refers to a solid or liquid ingredient that is used to impart a sweet taste to food or drug product. Sweeteners are often classified as either nutritive (caloric) or non-nutritive (non-caloric), natural or synthetic. Examples of sweeteners include but are not limited to sucrose, dextrose, lactose, glucose, advantame, sorbitol, mannitol, liquid glucose, honey molasses, saccharin, sucralose, rebaudioside A stevia, rebaudioside M stevia, stevioside, mogroside IV, mogroside V, alitame, saccharin, neohesperidin dihydrochalcone, cyclamate, neotame, N-[3_(3-hydroxy-4-methoxybenzylyl) propyl]-L-α-aspartyl]-L-phenylalanine 1-methyl ester, N-[3-(3-hydroxy-4-methoxyphenyl)-3-methylbutanyl]-L-α-aspartyl]-L-phenylalanine 1-methyl ester, N-[3-(3-methoxy-4-hydroxyphenyl) propyl]-L-α-aspartyl]-L-phenylalanine 1-methyl ester, curculin, cyclamate, aspartame, acesulfame potassium and others or mixtures thereof.

The term "colorants" and variations thereof generally refers to any dye, pigment, or other substance made by a process of synthesis or similar artifice, or extracted, isolated, or otherwise derived, with or without intermediate or final change of identity, from a vegetable, animal, mineral or other source and that, when added or applied, can impart color to a food, drug, or cosmetic or to the human body. Color makes products attractive, appealing, appetizing, and informative. Examples of colorants include but are not limited to Brilliant blue FCF, Indigotine, Alphazurine FG, Indigo, Indanthrene blue, Resorcin brown, Fast green FCF, Alizarin cyanine green F, Quinizarine green SS, Pyranine, Dibromofluorescein, Diiodofluorescein, Erythrosine yellowish Na, Copper phthalocyanine, Erythrosine, Ponceau SX, Lithol rubin B, Lithol rubin B Ca, Toney red, Tetrabromo fluorescein, Eosine, Tetrachlorotetra-bromofluorescein, Yellow Iron Oxide, Ultramarine Blue, Zinc Ferrite, Chromium Oxide Green, Titanium Dioxide, Zinc Oxide, Phloxine, Helindone pink CN, Brilliant lake red R, Acid fuchsine, Lake bordeaux B, Flaming red, Alba red, Allura red AC, Alizurol purple SS, Alizarin violet, Tartrazine, Sunset yellow FCF, Fluorescein, Napthol yellow S, Uranine, Quinoline yellow WS, Quinoline yellow SS and others or mixtures thereof.

The term "opacifying agents" and variations thereof generally refers to particles that scatter and reflect some of the incident light. Incorporated into drug formulations to improve the stability of light sensitive drugs, opacifying agents impart a "milky" or "lotionized" appearance to a liquid product. Examples of opacifying agents include but are not limited to aluminum stearate, calcium carbonate, calcium silicate, titanium dioxide, zinc acetate and others or mixtures thereof.

The term "matrix" or "film matrix" and variations thereof generally refers to the polymer component or mixture of polymers, which creates the film-forming matrix supporting the API within the oral film dosage form.

The term "residence time" and variations thereof generally refers to a time necessary for complete erosion/disintegration of the dosage form.

The term "delayed flavor release" and variations thereof generally refers to the release of all or a portion of flavor at times much later than the time of dosage form administration.

The term "emulsion" or "emulsified" and variations thereof generally refers to a system containing two immiscible liquids or more in which one is dispersed as very small droplets or globules throughout the other. For example, an emulsion may be water-in-oil or oil-in-water.

The term "Solvent Based Oral Film or SBOF" refers to the use of organic solvent to make the OF blend. The organic solvent is preferably selected from the group comprising highly volatile organic solvents but are not limited to ethyl acetate, acetone, methyl ethyl acetone, short-chain alcohols having 1 to 6 carbon atoms, in particular such as methanol, ethanol, and propanol including 1-propanol and 2-propanol. The organic solvent may also be a mixture of different organic solvents.

The term "Aqueous Based Oral Film or ABOF" refers to the use of water as a solvent to make the OF blend.

The term "film former polymers" refers to water-soluble or water dispersible polymers of common pharmaceutical use that conform to the required properties, including, but not limited to, film instant hydration potential, mucoadhesion and solubility over time. Examples of film forming polymers include cellulose derivatives, polyvinyl alcohol, polyvinyl pyrrolidone, polyethylene oxide, starches, polyacrylates, gums (xanthan gum, arabic gum, guar gum, etc.) and/or mixtures thereof. Film forming polymers may be used in combinations chosen based on the desired characteristics of the delivery form (e.g., rapid disintegration, higher mucoadhesion, longer residence time, etc.). Some of the film forming polymers may also act as emulsifier, and or viscosity modifier and or solubilizer.

The term "mouthfeel" generally refers to a variety of perceived qualities relating to texture and consistency, and most notably within the context of this disclosure to graininess (i.e., the extent to which the films can be perceived to contain grainy particles), and to the overall subjective perception of the subject to which the film is orally administered. To assess mouthfeel, the following methods may be used. Tactile evaluation: This involves physically manipulating the product in the mouth, such as by biting, chewing, or swirling it around. This can give you an idea of the texture, consistency, and viscosity of the product. Sensory evaluation: This involves evaluating the perception of the product in the mouth. This can include evaluating the presence of various sensations such as creaminess, smoothness, and astringency. Chemical evaluation: This involves analyzing the product to determine its chemical properties such as pH, viscosity, and temperature. Structural evaluation: This involves analyzing the structure of the product. This can include evaluating the size, shape and the distribution of the particles in the product.

The term "water soluble polymers" and variations thereof generally refers to water soluble polymers and, thus, modify the physical properties of aqueous systems in the form of gelation, thickening, or emulsification/stabilization that can be employed in the disclosed films and include water soluble cellulose derivatives, including hydroxypropylmethyl cellulose, hydroxyethyl cellulose, hydroxypropyl cellulose; polyvinyl pyrrolidone (PVP); copovidone (a copolymer of 1-vinyl-2-pyrrolidone and vinyl acetate); other copolymers of vinyl pyrrolidone; other polymers or copolymers of substituted vinyl pyrrolidone; derivatives of polyvinyl pyrrolidone; polyethylene oxide, carboxymethyl cellulose; polyvinyl alcohol; natural gums, including xanthan, tragacanth, guar, acacia and arabic gums; and water soluble polyacrylates. Combinations of these water-soluble polymers or other water-soluble polymers can also be used. Examples of substituted vinyl pyrrolidones include but are not limited to N-vinyl-3-methyl-2-pyrrolidone, N-vinyl-4-methyl-2-pyrrolidone, N-vinyl-5-methyl-2-pyrrolidone, N-vinyl-5,5-dimethyl-2-pyrrolidone, N-vinyl-3,3,5-trimethyl-2-pyrrolidone and others. Examples of monomers that can be copolymerized with vinyl pyrrolidone or substituted vinyl pyrrolidones include vinyl aromatic monomers such as styrene, and acrylate or methacrylate monomers such as methyl methacrylate and 2-dimethylaminoethyl methacrylate The term "breath freshening agents" or "breath freshener" and variations thereof generally refers to breath freshening agents such as spearmint oil, cinnamon oil, peppermint oil, clove oil, menthol, etc. Other potential breath freshening agents include zinc compounds, chlorhexidine gluconate, enzymes and probiotics.

The terms "surfactant" and "polyalcohol" are intended to have their ordinary meanings. Specifically, the term "surfactant" is intended to mean an amphiphilic compound that lowers the surface tension of a liquid, the interfacial tension between two liquids, or the interfacial tension between a liquid and a solid. Surfactants are also distinguishable based on their HLB "Hydrophilic-lipophilic balance", a measure of the degree to which it is hydrophilic or lipophilic. Common examples of surfactants include but not limited to polysorbates, sorbitan ester, polyoxylglycerides and propylene glycol laurates.

Polyalcohols, also known as polyhydric alcohols, are a class of compounds that contain multiple hydroxyl groups (—OH) in their molecular structure. For example, erythritol, one of the polyalcohols, has the chemical formula $C_4H_{10}O_4$. It is made up of four carbon atoms, ten hydrogen atoms, and four oxygen atoms. Another example is xylitol, which has the chemical formula $C_5H_{12}O_5$. It is made up of five carbon atoms, 12 hydrogen atoms, and five oxygen atoms. Common examples of polyalcohols or sugar alcohols that are eliminated in the disclosed films include but are not limited to glycol, glycerol, erythritol, threitol, arabitol, xylitol, ribitol, mannitol, sorbitol, galatitol, fucitol, iditol, inositol, volemitol, isomalt, maltitol, lactitol, maltotritol and maltotetraitol.

The products, compositions and processes of the present disclosure provide for technology that mitigates bitter and unpleasant aftertastes and generally improves the flavor profile of oral dosage forms.

The products, compositions and processes of the present disclosure rely on flavoring agent entrapment and methods of making thereof. The compositions have an effective amount of at least one free flavoring agent, resin entrapped flavoring agent and a bad taste active ingredient in an oral dosage form. The flavoring agent compositions are dry, liquid or a combination of both.

The compositions of the present disclosure cover or at least partially mitigate the perceived aftertaste and provide delayed flavors release thus making a relay of the initial flavor release, hence mitigating the perceived undesired aftertaste that occur after the stimulus has been removed from the oral cavity.

In another aspect of this disclosure, the method uses the resin entrapment to prevent at a certain extent the flavoring agent evaporation and provide desired flavor release.

The entrapment of the flavoring agents inside resin pores, make them more concentrated which is favorable to make a potent impact on taste buds receptor response when the flavoring agents are released.

According to embodiments, the bad aftertaste of an active ingredient and or one of the ingredients of the formula is the consequence of some taste stimuli that might hang around the buccal environment and can be covered with suitable flavoring agent(s) released from the resin complex at timing suitable to overcome any bad aftertaste and at a specific rate to maintain the right flavoring intensity profile during the time. The technology finds its application within the pharmaceutical industry as well as in food industry, in liquid systems, in semi-solid systems as in solid systems. It is disclosed the use of flavoring agent entrapment inside resin beads be used to address the bad aftertaste or to bring to the desirable flavor profile a formula (drug or food) of no taste.

According to embodiments, it is disclosed a method or formulation for mitigating perceived taste profile of an active upon intake of an OF containing such active in the mouth of a subject. The OF containing the active is typically dissolved, disintegrated and/or bioeroded upon contact with the saliva in a subject's buccal cavity.

According to embodiments, using resin flavoring agent entrapment in OF allows the mitigation of the perceived undesired aftertaste of a cannabinoid-containing OF while improving the control of the flavor profile of the product.

The most notable cannabinoid is the phytocannabinoid tetrahydrocannabinol (THC), the primary psychoactive compound in cannabis. There are at least 113 different cannabinoids isolated from cannabis plant, exhibiting varied effects.

Cannabinoids are active with a generally strong taste profile. The potentially unpleasant taste of a cannabinoid when taken orally is derived from the cannabinoids themselves as well as the terpenes and flavonoids present in the cannabinoid extract or distillate as a result of the various extraction methods used for extracting cannabinoids from the cannabis or hemp plants.

In addition to its strong and potentially undesirable taste, cannabinoids and their coextracted components have a pronounced aftertaste profile that lasts beyond the dissolution, disintegration or bioerosion period. This lasting taste is problematic, mainly for cannabinoid consumers that find such taste unpleasant. Hiding this taste is a challenge for much of the edible cannabis industry; however, hiding the taste of cannabinoids contained within for instance a brownie is markedly easier due to the low concentration of cannabinoid within the holding or loading media. To the contrary, masking the unpleasant taste of cannabinoids and their co-extracted compounds in an OF is challenging due to its very high concentration relative to the film's size, which according to some embodiments weigh between 30 and 250 mg. As such, the content of cannabinoids, cannabinoid distillate, cannabinoid co-extracted oil or resin may reach 50% or more of the film composition, thus highly constraining the amount of taste masker one is able to use. In addition, most taste maskers are very poor in their ability to mask or minimize the active or cannabinoid aftertaste.

As contemplated for use herein are antihistamines such as loratadine (available as Claritin®), astemizole (available as Hismanal™), nabumetone (available as Relafen®), and Clemastine (available as Tavist®).

As contemplated for use herein are insomnia medications. The method and formulation disclosed herein is particularly suitable for formulating unpleasant tasting insomnia medication such as eszopiclone (available as Lunesta®).

The flavor taste profile or the time-intensity profile of flavoring agent(s) encompass the reaction time, taste intensity, and duration of the taste(s). Time-intensity profile of flavoring agent(s) reflects the kinetic energy profile of flavoring agent(s) release from its presentation form. Flavoring agent(s) are introduced in the dosage form as resinate (entrapped in resin), polymer encapsulation, free form (non-entrapped, non-encapsulated), polymer encapsulation of both flavoring agent and the active of bad taste or entrapment of both inside the resin, or introduced as a combination of all previously discussed forms or others discussed in the art.

Taste buds are located on the top of the tongue and the soft palate as reported in the art, accordingly the ideal location to place the OF will be top of the tongue where the sensory impact of the flavoring agent will be the quickest and greatest, especially if the OF matrix has shorter disintegration time. Generally, OFs that dissolve more rapidly require less flavoring agent than those that dissolve slowly. This trend is related to the residence time of the active in the buccal environment and the ability to mask the taste of the active with a sufficient amount of flavoring agent. Mammals have a limited amount of taste buds, the receptors of which are saturable. Thus, after a certain limit, adding more flavoring agent to cover an unpleasant taste will have no effect. According to embodiments, OF formula with a reservoir system (coated encapsulated flavoring agent) that will help control release and presence of flavoring agent over time to keep the taste buds under flavor stimulation while the active is present in the mouth to overcome the bad or unpleasant taste are disclosed herein.

According to embodiments, the resin entraps the active and mitigates its unpleasant taste. The amount of resin used may be equivalent from half to 5 times the amount of active. The amount of resin may affect the active's pharmacokinetic profile.

The resinate of flavoring agent(s) when used to cover the aftertaste of the API and to maintain the flavor(s) profile will not affect the active's pharmacokinetic profile. In parallel, when a free flavoring agent(s) (not entrapped by the resin) is combined with resinate of flavoring agent(s) to mask active bad taste, this combination will not impact the active's pharmacokinetic profile.

According to embodiments, the presence of both forms of flavoring agent, namely as non-entrapped (free ready to use) and entrapped with resin (resinate) is beneficial to counteract the bad taste of the active due to its release in the buccal environment. In addition, the presence of the dual forms will continue to cover the active's aftertaste that persistently remains in the mouth after the active has been swallowed.

In one embodiment, the resinate can be prepared separately and introduced to the solvent for blending and continued formulation.

In another embodiment, the resin, the flavoring agent and solvent can be added simultaneously. It is preferable however to add the resin and flavoring agent before adding the polymers.

In some embodiments, an oral film matrix system is present. During the blending step, the resin and the flavoring agent entrapment are performed in the blending solvent or separately by wetting only the resin with liquid containing flavoring agent(s) for a certain period of time then introduced to the film blend. Further additions may include but are not limited to API(s), surfactant(s), plasticizer(s), sweetener(s), pore former(s), filler(s) and dye. A variety of optional components and fillers also may be added to the oral films.

In the embodiment above, it is preferable to avoid the use of components that are known to be complexed by the resin. It is desirable to add the thickening and film forming agent(s) at the later stage. For film technology generally, the addition of a thickening agent or the main film former polymers before the addition of resin and flavoring agent may interfere with their complexation (entrapment).

The use of resin entrapment as a carrier for flavoring agents is not sensitive to the shear process since the resin beads are not soluble in the processing media and will maintain their integrity during the mixing and the transfer. The advantage is that the resin's diameter is not proportional to the delay of flavoring agent release as it is in encapsulation technology, in addition resin entrapment as a carrier for flavoring agents is not affecting active drug uniformity of content and can be introduced in monolayer OF or more than one layer of oral film.

When the blend builds up a texture and all polymers are dissolved, the deaeration stage will be the end of the blending. The film will be coated and dried to generate oral films.

Insoluble flavoring agents cannot be used to cover the aftertaste using the resin entrapment concept. As discussed throughout, the use of smaller resin particles will prohibit the burst release as seen with larger resin particles.

The presence of ingredients in the blend that have high affinity and selectivity to the resin may reduce the efficacy of flavoring agent's entrapment and failure to cover the aftertaste.

The aftertaste coverage may depend on the residence time of the matrix: the longer the residence time, the higher the likelihood of the active aftertaste being perceived and the higher the likelihood for the resin flavoring agent complex to last in the buccal environment and cover the aftertaste. If the residence time of the film is shorter, the chance for the resin flavoring agent complex to reside in the mouth are low, hence there will be a higher likelihood that the active aftertaste to be perceived.

Complexation of the active agent in this disclosure can be useful in keeping the active agent separate from the various forms of additive flavoring agent. Complexation can thus avoid incompatibility of the two components of an OF.

In the buccal environment, the film matrix disintegration and hydration helps release both the API and resin flavoring agent complex. The result is that the taste will be covered two fold: masked initially by the free flavoring agent and then the aftertaste will be covered with the complexed (entrapped) flavoring agent that is exchanged in the media.

In certain embodiments, the disclosed films may include a plasticizer. The term "plasticizer" refers to a component that reduces the glass-transition temperature of the film forming polymers (e.g., the water-soluble polymer or water-soluble polymers in the film). The plasticizer increases flexibility, enhances elasticity and reduces brittleness of the film. Examples of plasticizers that can be used in the disclosed film oral dosage forms include but are not limited to triacetin, triethyl citrate, tributyl citrate, acetyl tributyl citrate, acetyl triethyl citrate, trioctyl citrate, acetyl trioctyl citrate, trihexyl citrate, dibutyl sebacate, etc. Plasticizers may be added in an amount up to 25% of the total mass of the film oral dosage form, such as from 0.5% to 25%, 1% to 20%, 2% to 15% or 5% to 10%.

The amount of drug that can be incorporated in the film oral dosage forms disclosed herein is generally from 0.01% to 50% by total weight of the film, such as 1% to 40%, 2% to 30%, or 5% to 20% by total weight of the film.

An adsorbent in pharmaceuticals is a substance that is used to remove impurities, toxins, or other unwanted compounds from a solution. Adsorbents work by binding these compounds to their surface, effectively removing them from the solution. Polymeric resins, such as cellulose, polystyrene, and polyacrylate can be used as adsorbents for specific types of impurities. Other common adsorbents used in pharmaceuticals include but are not limited to silica gels, alumina and clay minerals. Hydrophobicity of adsorbent is important in selecting a suitable type of adsorbent according to the chemical nature of the target compounds.

Insoluble flavoring agents cannot be entrapped with resins or other adsorbents. The flavoring agent must be dissolved in the loading media. In contrast, flavoring agents that are soluble in organic solvent(s) can be used with the applied organic solvent(s) for the entrapment step. As above, an OF matrix manufactured in a water-based and/or in an organic solvent will allow the flavoring agent(s) to be entrapped with resin in liquid phase of water and or in organic solvent depending on the solubility of the flavoring agent.

The strength of interaction between flavoring agents and chain groups of resins or other absorbent affects the loading percent of the flavoring agent during the entrapment step and will later affect their release (regeneration of the resin.) A highly water-soluble flavoring agent is likely to be subject to ion exchange resin for entrapment and therefore the interaction is mainly with ionic bonds between the charged groups of flavoring agents and an ion exchange resin support carrying the opposite charge.

In contrast, the hydrophobic (non-polar) flavoring agent that are liquid or soluble in their solvent is likely to be subject to adsorb with mainly hydrophobic groups on their main chain, therefore the more hydrophobic the group chain of resins makes the hydrophobic flavoring agent adsorbed very strongly. In parallel, the ionic flavoring agent has a degree of hydrophobicity that increases when pH of loading media is such favorable for increasing the uncharged part of the flavoring agent, and when the compound is zwitterionic (both acidic and basic functional groups coexist on the chemical entity) the hydrophobicity will increase around isoelectric point (pH at which a molecule or surface carries has neutral net electrical charge.)

As mentioned before, ionizable flavoring agents are candidates for entrapment by the ion exchange resin. The polymers that contain appropriately substituted acidic groups are for example but not limited to carboxylic and sulfonic for cation exchangers; or basic groups, such as but not limited to quaternary ammonium group for anion exchangers. In aqueous media, ion-exchange resins are generally classified as strong exchangers where the exchange with counter ions is independent of the solution pH or weakly dissociated exchangers where the exchange with counter ions depends in part on the solution pH. The release of entrapped ionic flavoring agents from the resinate depends upon the presence of an exchangeable ion in the release medium, therefore the ionic group chains of the resin must have higher affinity for the counter ion in solution compared to the entrapped ion in the resin.

Strong acid cation exchange resins and strong base anion-exchange resins are fully hydrated so they dissociate easily; and the ions associated with the functional group are always free to exchange with ions of like charge in the solution being processed. Consequently and as above, the exchange capacity of strong resins is independent of the solution pH. Strong ion exchange resins will release the entrapped ionic flavoring agent relatively slower than the weak exchange resins in the presence of counter ions. This is because the bonding of strong ion exchange resins with the ionic flavoring agent is strengthened by ionization of the ion exchange resin group and will release independently from the pH or the presence of counter ions.

Regarding the resinates of weak cation exchange resins, the degree of dissociation of a weak acid resin is strongly influenced by the solution pH. At a pH below resin chain group pKa (the pH value at which ionisation becomes effective), the bonding with the cationic flavoring agent is weak due to the non-ionisation of anionic group of the resin. The entrapped cationic flavoring agent is released similarly as without resin, indicating no significant entrapment. The same occurs for the weak anion exchange resin at pH close or above their pKa; there will be weak bonding of the anionic flavoring agent with the resin due to the non-ionisation of cationic groups of the latter. Flavoring agents are released similarly as without resin, indicating no significant entrapment.

When the pH of the media is close or above the resin pKa, weak cation exchange resins undergo ionization thus producing strong interactions with cationic flavoring agents within the resinate particles and the release of the entrapped flavoring agent becomes relatively slower compare at acidic pH condition. The release of the flavoring agent could be enhanced by the presence of another cationic ingredient or acidifying agent in the film formula that are released during film disintegration to create micro-environment pH and to be exchanged with the cationic flavoring agent. For OF formulation that uses liquid blending, counter ions that can enhance flavoring agent exchange from the ion exchange can be introduced in different film layers that does not contain a resinate of the flavoring agent to avoid early release of the flavoring agent during OF blending.

Weak anion exchange resins at pH below pKa of resin chain group behave like weak cation exchange resins (at pH above their pKa) in that the ionization produce strong interactions with anionic flavoring agent thus favoring more entrapment.

Based on above and due to the fact that saliva medium is of pH 6.7 and does not have enough counter ion (cation concentration of 40 mq/liter), the release of ionic flavoring agent could be minimal and/or spread over a long period of time. Weak ionic resin exchangers could be a candidate for flavoring agent entrapment that will be released to cover bad aftertastes. This may be accomplished by the use of a counter ion in the OF formula to modulate the release of flavoring agent during OF disintegration. This may apply to weak cation exchange resins with pKa of the chain group below the pH of saliva, and apply also to weak anion exchange resins with a pKa of the chain group close or above the pH of saliva. The selection of the above conditions are based on the kinetic profile of the flavoring agent release, when the resins tend to be in non-ionisable form (less interactions with the entrapped ionic flavoring agent), they will begin releasing the flavoring agent at a rate that is not favourable to cover the bad after taste of the drug, and for that reason we have to modulate the release rate with adding ions of opposite charge to be exchanged with the resin ionic group chain (beside the counter ions from the saliva) to manage the flavoring agent release and to cover at the right time the bad after taste of drugs.

Multilayer OFs with flavoring agent resinate and counter ion(s) are useful to design a custom release profile of the ionic entrapped flavoring agent. Other factor(s) need to be considered like the disintegration time of the OF layer containing the counter ion(s) and to make it available at the time of release of the resinate containing the ionic flavoring agent.

Resin exchange rate is affected also by the electrolytes that are naturally present in the saliva (competing ions). These electrolytes diffuse by concentration gradient from the media into the resin and hence the release rate of the ionic flavoring agent will increase.

Preferable flavoring agent release from the resin would enhance the main flavor profile that cover the initial bad active taste. The flavoring agent resinates have a purpose of mitigating active aftertaste and should cover in the first minutes following drug release in the buccal environment and continue to release for at least ten minutes following the total active release. Due to the limited amount of saliva (limited amount of electrolytes) and the delay that may be created by film disintegration to render the elution of the flavoring agent faster, the exchange of ionic flavoring agent with the counter ion inside the resin may not have chance to occur and to release the entrapped flavoring agent at the right timing. To better address the above-mentioned timing goal, it is preferable to simply use the uncharged resin where a counter ion is already attached on its chain group. With the weak interactions and steric hindrance properties imposed by the resin polymer network, the delay to create flavoring agent release by diffusion outside the resin is just enough to mitigate the active bad aftertaste.

Said uncharged forms are resins provided already with their counter ion; like H form of acid resin or OH form of basic resin. These unsalted forms (H form or OH form) make the ionic association of the ionic flavoring agent unlikely, therefore the physical entrapment of the flavoring agent into the resin network combined with the contribution of weak interactions like coordination bounds, hydrogen, Van der Waals bonds, and hydrophobic interactions of the flavoring agent hydrocarbon radicals all together can simultaneously overwhelm the contribution of the ionic interaction of the ion exchange resin itself.

Flavoring agents that are soluble in the loading media regardless of their degree of ionisation can penetrate the resin by diffusing through the pores, be entrapped in the resin structure, or be bound via hydrophobic interactions between their non-polar part and the hydrophobic matrix of the ion resin exchanger. The release from the resinate of the flavoring agent will be by diffusion in a fairly consistent manner.

The affinity of a flavoring agent to the resin is a product of multiple factors: the type of functional groups, the type of resin matrix and the degree of cross-linkage. The degree of cross-linkage generally determines the extent of swelling and shrinkage of ion-exchange resins. This is related to the percent of copolymerization and mechanical resistance due to volume change. For example, if the resin is less cross-linked it will favour the exchange of larger molecules through a porous resin matrix.

Another aspect to consider concerning resin affinity for the flavoring agent is the ion exchange capacity expressed by the number of ionic groups per unit of weight or volume. This affinity depends on accessibility of the functional groups for the flavoring agent of interest, resin swelling affecting the rate of resin hydration, the rate of exchange and capacity of the resin to entrap large molecules.

The flavoring agent entrapment in the resins depends on the type of resin, the preparation conditions of such and the type of flavoring agent used. Large flavoring agent molecules give lower loadings because of steric restrictions. The content of the resinate of flavoring agent usually decreases with the increasing degree of cross-linkage of the resin. The effect of particle size is less pronounced except for highly cross-linked resins where the flavoring agent content per resin increases with decreasing particle size.

For film technology, the addition of thickening agents or the main film former polymers before the addition of resin and flavoring agent may interfere with their complexation (entrapment).

The presence of ingredients in the blend that have high affinity and selectivity to the resin may reduce the efficacy of flavoring agent's entrapment and failure to cover the aftertaste.

The aftertaste coverage might depend on the residence time of the matrix. Generally, the longer the residence time, the longer the resin flavoring agent complex remains in the buccal environment and will have a chance to cover the aftertaste. If the residence time of the film is shorter, the resin flavoring agent complex generally resides in the mouth for less time.

Most bitter drugs have amine and amide functional groups such as alkaloids and long chain organic substances with nitrogen in their structures, like peptides with a high proportion of hydrophobic amino acids. The use of a cation exchange resin will be of double benefit: to entrap the bitter drug (taste masking of cationic nitrogen groups) and to entrap the flavoring agent to cover the bad aftertaste. Considering the pH of the saliva (neutral), the resin will be ionic which is favorable for both the drug and the ionic flavoring agent entrapment. Since the resinate of the flavoring agent is less strong compare to the one with the bitter drugs, there will be less drug release in the neutral pH compare to the flavoring agent release, so as the result the entire bitterness will be mitigated in the buccal environment.

Other groups of drugs like CBD that are neither amine nor amide are able to use anionic exchange resins to avoid any drug competition when loading or complexing the flavoring agent in the resin.

Conventional oral film additives, other than surfactants and polyalcohols, can be added as needed or desired, generally in amounts conventionally employed. Examples of such additives include artificial sweeteners such as sucralose, aspartame, acesulfame potassium and monoammonium glycyrrhizinate, natural sweeteners such as sucrose and fructose; flavoring agents such as menthol, various fruit flavors (e.g., cherry, grape, orange, etc.) or various mint flavors (e.g., spearmint, peppermint, etc.); colorants; opacifiers (e.g., titanium dioxide); and antioxidants (e.g., butyl-hydroxytoluene).

Other additives may also be incorporated in amounts that do not adversely affect film properties or film stability. Specifically, any such additives must not cause undesirable softening of the film and subsequent loss of dimensional stability, degradation of the active ingredient(s), or induce undesirable aesthetics such as discoloration of the film or noticeable segregation and agglomeration of film components.

The present disclosure encompasses the entrapment of flavoring agent with the use of resins to cover the aftertaste and/or provide delayed flavoring agent(s) release. This disclosure is applicable to artificial flavors, natural & artificial (N&A) Flavors, natural-type flavors and WONF (With Other Natural Flavors). The disclosure applies to flavoring agent(s) with or without a flavor enhancer(s) or bitter taste masker(s).

To reside inside the resin, the flavoring agent(s) must be liquid or a solid state that is soluble, emulsified, or suspended in the blending media.

To cover the aftertaste of pharmaceutical drugs, it is convenient to use hydrophobic flavoring agents that elute from the resin at a lower rate, as well the use of flavoring agents with high affinity to the resin inner structure.

One critical parameter of the disclosed formulation and method disclosed herein lies in the ability of the flavoring agent to be soluble in loading media. The entrapment of flavoring agents disclosed herein will not function as disclosed herein with flavoring agents that are insoluble or insolubilized/suspended in the loading media due to the required physical entrapment of the flavoring agent in the resin's pores. Physical entrapment of the flavoring agent is not possible when the nature of the flavoring agent renders it insoluble in the loading media.

Some elements that should be considered for the flavoring agent's entrapment with the resins are discussed the paragraphs that follow.

According to embodiments, the rate and completeness of flavoring agent desorption in vivo will be controlled by the diffusion rate of the flavoring agent through the polymer phase of the resin; usually a function of molecular weight, the selectivity of the flavoring agent for the resin inner structure and the concentration of electrolytes in the desorption environment particularly when the flavoring agents are ionizable.

The methods for determining the diffusion rate of flavoring agents in oral films are similar to those used for active ingredients. However, there are some differences in the testing methods and the parameters being measured depending on the nature of the flavoring agents.

The methods for testing the diffusion rate of flavoring agents in oral films include: In-vitro release testing: This method involves immersing the oral film in a buffer solution and measuring the amount of flavor released over time using analytical techniques such as sensory analysis, GC-MS or HPLC. Oral cavity simulation: This method involves using an apparatus that simulates the conditions of the oral cavity, to measure the amount of flavor released from the oral film over time. In-vivo testing: This method involves administering the oral film to animals or humans and measuring the perception of the flavor over time. Diffusion coefficients: This method involves measuring the diffusion coefficient of the flavoring agent in the oral film. The diffusion coefficient can be determined by measuring the release rate of the flavoring agent from the oral film and using the Fick's second law of diffusion.

It is important to note that the diffusion rate of flavoring agents can be affected by various factors such as the chemical properties of the flavoring agent, the composition of the oral film, and the conditions of the environment.

According to embodiments, the flavoring agent to resin ratio needs to be optimal to ensure an ideal loading of the resin.

According to embodiments, the concentration and selectivity of competing entities in the loading media affect the rate and completeness of flavoring agent desorption.

According to embodiments, the pH of the loading solution in the case of ionizable flavoring agents and ions exchange resins may influence the loading of the flavoring agents to the resin (complexation). If the API of bad taste carries a charge, it is likely to have a pronounced bad taste. An uncharged API will have a less bad taste.

In one embodiment, a method of forming a film of the present disclosure includes combining the film formulation ingredients, employing water, a combination of water and water-miscible solvents such as short carbon chain alcohols (e.g., ethanol) or organic solvents alone or as a mixture. For example, the plasticizer and additives (e.g., sweetening agents, colorants, flavoring agents, and opacifying agents) can be dissolved or dispersed in a sufficient amount of solvent that is agitated to form a homogenous solution or suspension to which the water-soluble polymer(s) is (are) added. Heat, vacuum and agitation may be applied as needed during addition of the water-soluble polymer until a homogenous solution or homogenous suspension is obtained. Thereafter, the active ingredient(s) is (are) added, and the solution or suspension is cast or coated onto a carrier material and dried to form a film. Examples of suitable carrier materials include non-siliconized polyethylene terephthalate film, non-siliconized kraft paper, polyethylene-impregnated kraft paper and non-siliconized polyethylene film. The liquid film composition can be coated onto the carrier material using generally any conventional coating equipment, including knife-over-roll, extrusion die, reverse roll, or Meyer roll coating equipment.

Upon drying, the resulting solid film can have a thickness of generally 5 to 200 μm, such as 10 to 200 μm, 20 to 150 μm or 20 to 100 μm. The film can be cut into individual pieces having a suitable size to facilitate administration of a targeted dosage of active agent(s).

Example 1

Film oral dosage forms are prepared using the above-described processes and compositions listed in the following Table 1.

| Ingredients function | Compound | % Dry | % Wet |
|---|---|---|---|
| Blend solvent | USP Purified water | | 85.40 |
| Surfactant | Hydroxylated lecithin SOLEC S | 7.02 | 1.02 |
| Viscosity increasing agent/suspending agent | PGA LV (1) | 7.02 | 1.02 |
| Viscosity increasing agent/suspending agent | Xantham gum | 0.59 | 0.09 |
| Active pharmaceutical agent | CBD full spectrum | 12.68 | 1.85 |
| Sweetener and masker agent | Advantame | 0.05 | 0.01 |
| Film forming polymer | HPMC E15 | 3.90 | 0.57 |
| Flavoring agents to be entrapped | Peppermint oil 2:1 Eucalyptol | 14.63 | 2.14 |
| Stabilizer/bitter masker | Ascorbic acid | 1.76 | 0.26 |
| Plasticizer | Glycerine | 2.73 | 0.40 |
| Resin (carrier) | Resin amberlite IRP 64 | 7.80 | 1.14 |
| Film forming polymer | PGA LV (2) | 20.48 | 2.99 |
| Sweetener/pore former | Maltitol | 13.65 | 1.99 |
| Flavoring agent | I-Menthol | 2.93 | 0.43 |
| Masker | Bitter mask | 1.95 | 0.28 |
| Sweetener | Sucralose | 1.95 | 0.28 |
| Salt | NaCl | 0.88 | 0.13 |
| | Total | 100 | 100 |

Oral film blend prepared as per following:
1. Prepare aqueous solution using water, glycerin, hydroxylated lecithin SOLEC S. Mix the ingredient and continue for the next steps.
2. Add to the blend under stirring the CBD.
3. Add to the blend under stirring propylene glycol alginate low viscosity (PGA LV (1)) and Xanthan.
4. Prepare separately a premix (M) using flavoring agents mixture of peppermint oil and 1 Eucalyptol (2:1) and the AMBERLITE IRP64 resin (weakly acidic resin), leave the mix to stand for 2 hours without stirring.
5. Add premix (M) to the aqueous solution.
6. Add to the blend under stirring advantame, ascorbic acid, maltitol, I-Menthol, Bitter mask, Sucralose, and NaCl.
7. Add to the blend under stirring PGA (2) and HPMC E15.
8. When everything get well mixed and dissolved.
9. The final blend is deaerated then coated on film support (liner) and dried at 60 C for 90 minutes.

Example 2

Film oral dosage forms are prepared using the below described processes and compositions listed in the following Table 2.

Oral film blend F1 was prepared as per following:
1. Prepare aqueous solution using water, glycerin and maltitol,
2. Keep aqueous solution under mixing and add flavoring agents mixture of peppermint oil and 1 Eucalyptol (2:1),
3. Add under mixing the AMBERLITE IRP64 resin (weakly acidic resin),
4. Add under mixing propylene glycol alginate low viscosity (PGA LV) and pullulan Oral film blend F2 was prepared as per following:
1. Prepare aqueous solution using water, glycerin and maltitol,
2. Prepare separately a premix (M) using flavoring agents mixture of peppermint oil and 1 Eucalyptol (2:1) and the AMBERLITE IRP64 resin (weakly acidic resin), leave the mix to stand for 2 hours without stirring
3. Add premix (M) to the aqueous solution
4. Add to the blend under stirring propylene glycol alginate low viscosity (PGA LV) and pullulan Oral film blend F3 was prepared as per following:
1. Prepare aqueous solution using water, glycerin and maltitol
2. Keep mixing and add flavoring agents mixture of peppermint oil and 1 Eucalyptol (2:1)

| | F1 | | | F2* | | | F3 | | |
|---|---|---|---|---|---|---|---|---|---|
| Compound | Mass (g) | % Dry | % Wet | Mass (g) | % Dry | % Wet | Mass (g) | % Dry | % Wet |
| USP Purified water | 44.00 | | 78.64 | 44.00 | | 78.64 | 44.00 | | 79.39 |
| PGA LV | 1.60 | 13.39 | 2.86 | 1.60 | 13.39 | 2.86 | 1.60 | 14.01 | 2.89 |
| peppermint oil 2:1 Eucalyptol | 1.00 | 8.37 | 1.79 | 1.00 | 8.37 | 1.79 | 1.00 | 8.76 | 1.80 |
| Glycerin | 1.20 | 10.04 | 2.14 | 1.20 | 10.04 | 2.14 | 1.20 | 10.51 | 2.17 |
| AMBERLITE IRP64 Resin | 0.53 | 4.46 | 0.95 | 0.53 | 4.46 | 0.95 | | | |
| Pullulan | 6.12 | 51.20 | 10.94 | 6.12 | 51.20 | 10.94 | 6.12 | 53.59 | 11.04 |
| Maltitol | 1.50 | 12.55 | 2.68 | 1.50 | 12.55 | 2.68 | 1.50 | 13.13 | 2.71 |
| Total Wet | 55.95 | 100.00 | 100.00 | 55.95 | 100.00 | 100.00 | 55.42 | 100.00 | 100.00 |
| Total Dry | 11.95 | | | 11.95 | | | 11.42 | | |

3. Add to the blend under stirring propylene glycol alginate low viscosity (PGA LV) and pullulan The three blends are coated and dried at 60 C for 60 minutes.

Tasting of the placebo films give the following results:

Film F1: the flavors are not perceived immediately even when if the film matrix start hydration, the taste sensation is perceived after a lag time of 1 minute.

Film F2: the flavors are not perceived immediately even when if the film matrix start hydration, the taste sensation is perceived relatively later than in film F1.

Film F3: the flavors are perceived immediately after matrix hydration.

Example 3

Bilayer oral film containing flavor resonates and counter ion are prepared using the below described processes and compositions listed in the following Table:

| Compound | Mass (g) | % Dry per layer | % Wet per layer | % Dry per bilayer | % Wet per bilayer |
|---|---|---|---|---|---|
| Bilayer oral film | | | | | |
| Active film layer | | | | | |
| USP water | 44.00 | | 73.42 | | 47.09 |
| PGA LV | 1.60 | 10.05 | 2.67 | 6.60 | 1.71 |
| Lecithin | 1.00 | 6.28 | 1.67 | 4.12 | 1.07 |
| THC | 1.00 | 6.28 | 1.67 | 4.12 | 1.07 |
| peppermint oil 2:1 Eucalyptol | 2.00 | 12.56 | 3.34 | 8.25 | 2.14 |
| Glycerin | 1.20 | 7.53 | 2.00 | 4.95 | 1.28 |
| AMBERLITE IRP64 Resin | 1.50 | 9.42 | 2.50 | 6.19 | 1.61 |
| advantame | 0.01 | 0.04 | 0.01 | 0.02 | 0.01 |
| Pullulan | 6.12 | 38.43 | 10.21 | 25.24 | 6.55 |
| Maltitol | 1.50 | 9.42 | 2.50 | 6.19 | 1.61 |
| Total Wet | 59.93 | 100.00 | 100.00 | | |
| Total Dry | 15.93 | | | | |
| Placebo film layer | | | | | |
| USP water | 25.00 | | 74.58 | | 26.75 |
| PGA MV | 0.40 | 4.81 | 1.19 | 11.65 | 0.43 |
| Glycerin | 0.80 | 9.62 | 2.39 | 13.30 | 0.86 |
| Pullulan | 6.12 | 73.56 | 18.26 | 125.24 | 6.55 |
| Maltitol | 1.00 | 12.02 | 2.98 | 14.12 | 1.07 |
| NaCl | 0.20 | 2.40 | 0.60 | 0.82 | 0.21 |
| Total Wet | 33.52 | 102.40 | 100.00 | | 99.79 |
| Total Dry | 8.32 | | | 100.00 | |

1. Prepare placebo film layer using water, glycerin, NaCl and maltitol. Mix the ingredients and continue for the next steps.
2. Add to the blend under stirring propylene glycol alginate medium viscosity (PGA MV) and pullulan.
3. The final blend is deaerated then coated on film support (liner) and dried at 68 C for 45 minutes.
4. Prepare active film layer using water, glycerin and lecithin. Mix the ingredients and continue for the next steps.
5. Add to the blend under stirring API.
6. Add to the blend under stirring propylene glycol alginate low viscosity (PGA LV) and pullulan.
7. Prepare separately a premix (M) using flavoring agents mixture of peppermint oil and 1 Eucalyptol (2:1) and the AMBERLITE IRP64 resin (weakly acidic resin), leave the mix to stand for 2 hours without stirring.
8. Add premix (M) to the aqueous solution.
9. Add to the blend under stirring maltitol and advantame.

10. The final blend is deaerated then coated on film placebo layer (first film layer) and dried at 68 C for 30 minutes.

The invention claimed is:

1. An entrapped flavor oral film, comprising an effective amount of at least:
   a. a free flavoring agent;
   b. a resin-entrapped flavoring agent prepared by pre-loading a hydrophobic flavoring agent into pores of a weak ion-exchange resin in a loading media to form a resinate complex; and
   c. an active agent;
wherein the hydrophobic flavoring agent is soluble in the loading media and entrapped within the weak ion-exchange resin in its un-ionized form;
wherein the resin-entrapped flavoring agent provides delayed release of the hydrophobic flavoring agent through diffusion from the resinate complex to mitigate perceived aftertaste occurring after initial taste masking by the free flavoring agent; and wherein said formulation at least partially mitigates the perceived aftertaste of the active agent and improves the taste of the oral film.

2. The oral film formulation of claim 1, wherein the active agent is a cannabis derivative.

3. The oral film formulation of claim 1, wherein said free flavoring agent is a liquid or a solid that is soluble, emulsified, or suspended in a suitable blending media for oral film formulations.

4. The oral film formulation of claim 1, further comprising a flavor enhancer in an amount of 0.1% to 5% by weight of the oral film.

5. The oral film formulation of claim 4, wherein the flavor enhancer is a yeast derivative.

6. The oral film formulation of claim 1, comprising an amount of resin, ranging from half to 5 times the amount of the active agent.

7. The oral film formulation of claim 1, further comprising a taste masker in an amount of 0.1% to 8% by weight of oral film, which improves the overall taste of the oral film.

8. The oral film formulation of claim 7, wherein the taste masker is a sweetener.

9. The oral film formulation of claim 1, further comprising a plasticizer in an amount of 1% to 24% by weight of the oral film, which improves the flexibility and mouthfeel of the oral film.

10. The oral film formulation of claim 9, wherein the plasticizer is polyethylene glycol, glycerol, triacetin, propylene glycerol and sorbitol, or a combination thereof.

11. The oral film formulation of claim 1, further comprising a counter ion, which modulates the release of flavoring agent during oral film disintegration.

12. The oral film formulation of claim 1, further comprising a film that is applied to the oral cavity of a mammal, optionally adhering to the tongue or buccal cavity of the mammal, and optionally dissolving within the oral cavity in less than about one or two minutes.

13. The oral film formulation of claim 1, wherein the amount of active agent incorporated is from 0.01% to 50% by total weight of the film.

14. The oral film formulation of claim 1, wherein said film is monolayer, bilayer or multilayer.

15. The oral film formulation of claim 1, wherein the resin-entrapped flavoring agent is released primarily by diffusion through the resin matrix over a period sufficient to mitigate the aftertaste of the active pharmaceutical ingredient.

16. The oral film of claim 1, wherein the active is present at a concentration of at least 50% by weight of the film and having an unpleasant taste.

17. An entrapped flavor oral film matrix system comprising:

an initial taste improver comprising free flavoring agent;

a secondary taste improver comprising a resinate formed by pre-loading a hydrophobic flavoring agent into pores of a weak ion-exchange resin in a loading media;

an unpleasant tasting active;

wherein the resinate is prepared by the combination of a resin and a flavoring agent in the blending solvent or separately by wetting only the resin with liquid containing the flavoring agent before being introduced to the film blend; and wherein the oral film matrix system at least partially mitigate the perceived aftertaste of the active agent.

\*  \*  \*  \*  \*